United States Patent [19]

Youngdale

[11] 4,022,904

[45] May 10, 1977

[54] COMPOSITION AND METHOD OF USE

[75] Inventor: Gilbert A. Youngdale, Kalamazoo, Mich.

[73] Assignee: The Upjohn Company, Kalamazoo, Mich.

[22] Filed: Dec. 8, 1975

[21] Appl. No.: 638,865

Related U.S. Application Data

[63] Continuation of Ser. No. 549,183, Feb. 12, 1975, abandoned, which is a continuation of Ser. No. 510,226, Sept. 30, 1974, abandoned, which is a continuation of Ser. No. 457,764, April 4, 1974, abandoned, which is a continuation of Ser. No. 386,537, Aug. 8, 1973, abandoned, which is a continuation of Ser. No. 328,875, Feb. 1, 1973, abandoned, which is a continuation of Ser. No. 34,856, May 5, 1970, abandoned.

[52] U.S. Cl. .............................................. 424/278
[51] Int. Cl.$^2$ ..................................... A61K 31/335
[58] Field of Search .................................. 424/278

[56] References Cited

OTHER PUBLICATIONS

Coppola, Chemical Abstracts 70:56161r, (1969).
Chemical Abstracts 64:16687a, (1966).
Jones et al., Nature, vol. 224, p. 83, Dec. 4, 1969.
Jones et al., Chemical Abstracts 71:111291f, (1969).

*Primary Examiner*—Norman A. Drezin
*Attorney, Agent, or Firm*—William G. Jameson; Sidney B. Williams, Jr.; John J. Killinger

[57] ABSTRACT

Pharmaceutical preparations in dosage forms and animal feeds (baits) consisting essentially of compatible, pharmaceutically acceptable carriers, oral and injectable, compounded with a sub-lethal, yet effective, amount of epichlorohydrin for inducing sterility in male mammals. Methods for preventing impregnation of females by male mammals which comprises administering systemically to male mammals a sterilizing amount of epichlorohydrin, also identified as γ-epichlorohydrin.

6 Claims, No Drawings

COMPOSITION AND METHOD OF USE

This is a continuation of application Ser. No. 549,183, filed Feb. 12, 1975 now abandoned, which is a continuation of application Ser. No. 510,226, filed Sept. 30, 1974, now abandoned, which is a continuation of application Ser. No. 457,764, filed Apr. 4, 1974 now abandoned, which is a continuation of application Ser. No. 386,537, filed Aug. 8, 1973, now abandoned, which is a continuation of application Ser. No. 328,875, filed Feb. 1, 1973, now abandoned, which is a continuation of application Ser. No. 34,856, filed May 5, 1970, now abandoned.

BRIEF SUMMARY OF THE INVENTION

This invention relates to pharmaceutical preparations and methods of use thereof. The pharmaceutical preparations are compounded with edible and injectable carriers to prepare baits, capsules, both hard and soft, suspensions, and injectables. The preparations contain an effective amount of epichlorohydrin for bringing about sterility in the male mammals, for example, monkeys, rats, hamsters and guinea pigs.

DETAILED DESCRIPTION

The active ingredient of the present invention, that is, epichlorohydrin, can be prepared by the reaction of 1,3-dichloro-2-propanol with sodium hydroxide as disclosed in Org. Syn., 3, 47 (1923).

The pharmaceutical preparations are prepared by mixing the epichlorohydrin with compatible, edible diluents, e.g., magnesium oxide, zinc oxide and aluminum oxide. (Compatible diluents are those which do not contain free hydroxyl or amino groups, that is, water, alcohols, sugars and the like are chemically incompatible with the active ingredient.)

Animal baits can be prepared by first micro encapsulating the epichlorohydrin by methods known to the art, e.g., coacervation and then mixing with animal bait carriers, for example, oatmeal or other cereal grains or proteinaceous foods, e.g., fishmeal and the like.

Parenteral forms are prepared by dispersing the epichlorohydrin in suitable fluid diluents, for example, paraffin, mineral oil, vegetable oils such as peanut oil, corn oil and cottonseed oil.

All dosage forms as heretofore described, contain from about 0.01 gram to about 2.5 grams of the epichlorohydrin per unit dose, but are not limited thereto, since within such range they include, for example, 0.5 gram, 1.0 gram, and 2.0 grams. Sterile parenteral forms for injection contain from about 0.5% weight/volume to 50% weight/volume of epichlorohydrin. For animal baits the concentration is from about 0.1% weight/weight to about 50% weight/weight of epichlorohydrin. These dosage forms provide, generally, the dosage range of essential active ingredient from about 0.1 to about 2.5 grams per day. The daily oral and parenteral doses for rendering a male sterile are approximately the same except for sustained parenteral dosage forms which contain from about 0.1 gram to 0.5 gram of epichlorohydrin per milliliter and are given once a month intramuscularly. The usual oral and parenteral forms are to be administered once per day or in the case of baits allowed to be fed ad lib.

Mature virgin male rats are checked for ability to mate by placement with immature female rats primed with gonadotropic factor of pregnant mare's serum. Those males which mate are used for subcutaneous injection or oral administration of the novel pharmaceutical preparations. The essential active ingredient is prepared as a 30 mg./ml. dispersion in 0.25% aqueous methylcellulose in sterile vehicle. This pharmaceutical composition is administered to each of three mature mating males, a half ml. per day subcutaneously or orally for 8 days. These treated males are exposed to receptive mature females for mating and mating is checked by the presence of sperm with or without a plug in the vagina of the female. Approximately ten days thereafter, the females are examined for the presence and number of implantation sites, and the ability of the pharmaceutical compositions to prevent impregnation by the mature male is shown by the absence of implantation sites at autopsy.

The following examples illustrate the manner and process of making and using the invention but are not to be construed as limiting.

EXAMPLE 1

Epichlorohydrin was prepared as a 3% sterile dispersion in 0.25% aqueous methylcellulose. One-half ml. was injected subcutaneously into each of three mating male rats for 8 days. Thereafter, the treated males were subjected to the aforesaid procedure to determine the ability of the preparation to prevent impregnation of female rats by the males, and the preparation was found to be effective.

EXAMPLE 2

An oral pharmaceutical preparation containing 1% of epichlorohydrin in 0.25% methylcellulose was administered orally to mating mature male rats daily for 7 weeks at a daily dose of 5 mg./rat. This preparation induced inability in the males to impregnate receptive females by the first week, and this infertility remained throughout the treatment. Post-treatment, the ability to impregnate receptive females returned the first week of post treatment and bred females had a normal number of implantation sites.

EXAMPLE 3

A soft gelatin capsule is prepared to contain 0.01 gm. of epichlorohydrin. An oral daily dose of 1 capsule is effective to prevent impregnation of a receptive female by mature male rats.

EXAMPLE 4

Cottonseed oil is used as a sterile vehicle to prepare a sterile dispersion of epichlorohydrin, 250 mg./ml. Injection of 1 ml. daily is effective to prevent impregnation of receptive female monkeys by a mature male. Other oils, such as peanut oil or mineral oil could also be used.

EXAMPLE 5

Cottonseed oil is used as a sterile vehicle to prepare a sterile dispersion of epichlorohydrin, 250 mg./ml. Injection of 1 ml. daily is effective to prevent impregnation of receptive female monkeys by a mature male. Ability to impregnate returns during the first week after cessation of treatment.

Additional embodiments of the present inventive concept are compositions, i.e., rations, for oral ingestion by rodents, especially rats, and methods of controlling rodent population, especially the rat population. Such rations contain the essential active ingredient and, in amounts that are attractive to the animals in the sense that they are not repelled thereby, edible dietary constituents such as protein, fat, carbohydrate, minerals, and vitamins.

The medicated ration must not repel the rodents although it does not necessarily have to attract in the sense of being absolutely preferred over other rations. Hence, the medicated ration retains the natural flavor of the dietary constituents after the essential active ingredient is incorporated therein. Such incorporation provides a final mixture or blend throughout which the active ingredient is uniformly distributed. Such active ingredient can be added to the ration by mixing both as solids or as liquids, by addition to a solid ration of the active ingredient itself, by adding the active ingredient in a compatible liquid which is then removed to leave a dry solid mixture, for example, a solution or suspension in chloroform, methylene chloride, or acetone; by adding the active ingredient in the form of coated particles or pellets, coated, for example, by coacervation with PVP, or by coating with an acetone solution of a oil-soluble type of PEG-ester. The final ration containing the coated particles or pellets is the preferred form because of its tendency to better mask any undesirable taste of the essential active ingredient. The rations contain the essential active ingredient in a concentration sufficient to control fertility or cause lesions in the excurrent duct (epididymal lesions) and permanent infertility in otherwise fertile male animals, especially rats, when they ingest the compositions in their usual manner of providing for their metabolic needs. Illustratively, most mature male rats that ingest an amount of the ration providing at least about 30 mg. per kilogram of rat body weight become irreversibly infertile as shown by epididymal lesions and by sterile matings with fertile females. As will be apparent, rats eating ad libitum will consume different amounts of the active ingredient-containing rations. Hence, to provide about 30 mg. per kilogram in a rat eating a smaller amount of the effective ration, a more concentrated ration must be provided than for a rat consuming a larger amount of the same ration. In the latter case, a less concentrated ration is operable. For example, in rats weighing about 200 to 250 gm. and consuming about 10 to 25 gm. of ration at one feeding, the ration may contain 0.075% by weight of the active ingredient. Thereby, the 250 gm. rat consuming 10 gm. of the treated edible preparation ingests 7.5 mg. of the active ingredient equivalent to about 30 mg. per kilo. With this same ration containing 0.075% active ingredient, a 200 gm. rat eating 25 gm. at one feeding ingests 18.75 mg. of the active ingredient, equivalent to about 93.75 mg. per kilo. Such variations will occur due to the eating habits of the rats. Hence, various embodiments of the rodent-control preparations are within the inventive concept provided they contain an effective amount of the essential active ingredient to cause the males to acquire the epididymal lesions of infertility.

The aforesaid embodiments of this inventive concept provide a method of controlling fertility of male rodents, especially rats, which consists essentially of providing in locales available to and frequented by said male rodents, rations supplying an effective amount of the compound epichlorohydrin for preventing impregnation of receptive sexually mature female rodents by the male counterparts thereof. Preferably, the rations supply to the recipient at least about 30 mg./kilogram of body weight thereof. At this level most rats acquire irreversible infertility and a reduction in rat population ensues in time. Expressed as percentage by weight of the edible composition, the active ingredient amounts to from about 0.05% to about 0.5%, such range being not limited thereto for it includes within the range the other percentages such as 0.1%, 0.2%, 0.3%, and 0.4%. A more concentrated preparation, say up to about 2% or even 5%, is satisfactory provided it is, upon use, diluted with the aforesaid edible dietary constituents to provide operative amounts of the essential active ingredient without wasting active material. These embodiments of the inventive concept are made available to the animals, especially rats, for control of the population thereof by placing the preparation in and about the locales available to and frequented by the rodents.

In accordance with these and other embodiments of the inventive concept, the following are additional examples of the manner and process of making and using the invention but are not to be construed as limitations.

EXAMPLE 6

A rat ration containing the usual dietary ingredients, protein, carbohydrate, fat, minerals and vitamins is medicated by incorporating therein a sufficient quantity of epichlorohydrin to provide a concentration of about 0.25% by weight. This ration is placed in and about a grain storage area where wild rats are observed and considerable loss of grain occurs. There follows a gradual reduction in rat population in the area such that contamination of the grain and loss thereof are both significantly reduced.

Although not necessary to the several embodiments heretofore described, other active ingredients can be included in the preparations and methods. The amounts of such ingredients are determined in reference to their known biological and physiological properties. Such ingredients are anticoagulant-rodenticides e.g., 2-diphenyl-acetyl-1,3-indandione, and its salts (U.S. Pat. No. 2,900,302), 3-(alpha-ethylbenzl)-4-hydroxycoumarin and its chloro derivative, 3-(alpha-ethyl-p-chlorobenzl)-4-hydroxycoumarin, 3-(alpha-acetonyl-4-chlorobenzyl-4-hydroxycoumarin, 3-(alpha-acetonyl-furfuryl)-4-hydroxycoumarin, 2-pivalyl-1,3-indandione, calcium salt of 2-isovaleryl-1,3-indandione and the like; stomach poisons, e.g., sodium fluoroacetate, alpha-naphthylthiourea, thallium sulfate, zinc phosphide, arsenic trioxide, strychnine, and red squill; estrogens, e.g., mestranol, ethinyl estradiol, diethyl stilbestrol, and chlorotrianisene; androgens, e.g., fluoxymestrone and methyltestosterone; and progestogens, e.g., melengestrol acetate, eithisterone, medroxyprogesterone acetate, and norethindrone.

Depending upon locale, e.g., farm, urban, business, and type of pest to be controlled and desired effect thereupon, these additional active ingredients are beneficial in controlling vertebrate pests, e.g., such as rats, gophers, dogs, hares and coyotes. In rat control the use of the additional anticoagulant active ingredient reduces the rat population sooner than expected. Similar beneficial effects attend the use of the additional stomach poison active ingredient.

EXAMPLE 10

A rat bait containing yellow corn meal is medicated by incorporating therein a sufficient quantity of epichlorohydrin to provide a concentration of about 0.25 percent by weight. This bait is placed in and about a grain storage area or meat packing plant where wild rats are observed and considerable loss of grain or meat occurs. There follows a gradual reduction in rat population in the area such that contamination of the grain and meat and loss thereof are both significantly reduced. Additional baits can be made from a mixture of oatmeal and dried fish meal; whole corn, oatmeal and dried fish meal; oatmeal and ground beef, or yellow cornmeal and ground beef.

I claim:

1. A method of rendering male mammals selected from the group consisting of monkeys, rats, hamsters, guinea pigs, gophers, dogs, hares and coyotes sterile which comprises administering systemically by oral or parenteral administration to said male mammals a sterilizing amount of epichlorohydrin.

2. The process of claim 1 wherein from about 100 milligrams to about 500 milligrams/kilogram body weight/day is administered.

3. A method of producing epididylmal lesions and infertility in male rodents which comprises supplying to said rodents in locales available to and frequented by said rodents a ration supplying an effective amount of epichlorohydrin for producing the lesions and infertility.

4. A method of claim 3 wherein the effective amount is at least about 30 mg./kg. of body weight of said male rodents.

5. A method of rendering male mammals selected from the group consisting of monkeys, rats, hamsters and guinea pigs sterile which comprises oral administration to said male mammals of a sterilizing amount of epichlorohydrin.

6. A method of rendering male mammals selected from the group consisting of rats, gophers, dogs, hares and coyotes sterile which comprises oral administration to said male mammals of a sterilizing amount of epichlorohydrin.

* * * * *

UNITED STATES PATENT AND TRADEMARK OFFICE
CERTIFICATE OF CORRECTION

PATENT NO. : 4,022,904
DATED : May 10, 1977
INVENTOR(S) : Gilbert A. Youngdale

It is certified that error appears in the above—identified patent and that said Letters Patent is hereby corrected as shown below:

On The Title Page,
In the references: "Jones et al., Nature, Vol. 224, p. 83, Dec. 4, 1969." should read -- Jones et al., Nature vol. 224, p. 83, 10/4/69 --.
In the Abstract: "γ-epichlorohydrin." should read -- α-epichlorohydrin. --.
Column 4, line 39: "ethylbenzl" should read -- ethylbenzyl --.
Column 4, line 41: "chlorobenzl" should read -- chlorobenzyl --.
Column 4, line 51: "eithisterone" should read -- ethisterone --.
Column 6, line 1: "epididylmal" should read -- epididymal --.

Signed and Sealed this

Thirty-first Day of August 1982

[SEAL]

Attest:

GERALD J. MOSSINGHOFF

*Attesting Officer*  *Commissioner of Patents and Trademarks*